United States Patent
Lin et al.

(10) Patent No.: US 9,439,948 B2
(45) Date of Patent: Sep. 13, 2016

(54) DEGRADABLE CAGE COATED WITH MINERAL LAYERS FOR SPINAL INTERBODY FUSION

(75) Inventors: Chia-Ying Lin, Ann Arbor, MI (US); Frank LaMarca, Ann Arbor, MI (US); William L. Murphy, Madison, WI (US); Scott J. Hollister, Saline, MI (US)

(73) Assignees: The Regents of the University of Michigan, Ann Arbor, MI (US); Wisconsin Alumni Research Foundation, Madison, WI (US)

( * ) Notice: Subject to any disclaimer, the term of this patent is extended or adjusted under 35 U.S.C. 154(b) by 1283 days.

(21) Appl. No.: 11/927,322

(22) Filed: Oct. 29, 2007

(65) Prior Publication Data
US 2008/0215093 A1 Sep. 4, 2008

Related U.S. Application Data

(60) Provisional application No. 60/855,235, filed on Oct. 30, 2006.

(51) Int. Cl.
*A61F 2/44* (2006.01)
*A61K 38/18* (2006.01)
(Continued)

(52) U.S. Cl.
CPC ......... *A61K 38/1875* (2013.01); *A61F 2/4455* (2013.01); *A61K 38/1825* (2013.01); *A61K 38/1841* (2013.01); *A61K 38/1858* (2013.01); *A61K 38/30* (2013.01); *A61B 17/7059* (2013.01); *A61F 2002/3008* (2013.01); *A61F 2002/30011* (2013.01); *A61F 2002/30013* (2013.01); *A61F 2002/30032* (2013.01);
(Continued)

(58) Field of Classification Search
CPC .................. A61F 2/4455; A61F 2002/30578; A61F 2002/30785; A61F 2002/30789; A61F 2002/30838
USPC ............. 623/17.11–17.16, 23.76; 606/87, 88
See application file for complete search history.

(56) References Cited

U.S. PATENT DOCUMENTS

| 4,355,429 A | 10/1982 | Mittelmeier et al. |
| 4,778,473 A | 10/1988 | Matthews et al. |

(Continued)

FOREIGN PATENT DOCUMENTS

| WO | 02/30337 A2 | 4/2002 |
| WO | 02/087475 A2 | 11/2002 |

(Continued)

OTHER PUBLICATIONS

Infuse Bone Graft, hftp://www.infusebonegraft.com.
(Continued)

*Primary Examiner* — Jan Christopher Merene
*Assistant Examiner* — Atiya Mahmud
(74) *Attorney, Agent, or Firm* — Quarles & Brady LLP

(57) ABSTRACT

A cage for facilitating fusion of bones, such as vertebrae, or fusion of adjacent bone surfaces is disclosed. In one form, the cage includes a plurality of spaced apart walls comprising a biodegradable polymeric material (e.g., polycaprolactone); an osteoconductive mineral coating (e.g., a calcium compound) on at least a portion of the walls; and a bioactive agent (e.g., a bone morphogenetic protein) associated with the polymeric material and/or the coating. The bioactive agent is present in amount that induces ossification between the bones or adjacent bone surfaces. The cage may also include a fixation plate connected to at least one of the walls.

32 Claims, 6 Drawing Sheets

(51) Int. Cl.
*A61K 38/30* (2006.01)
*A61B 17/70* (2006.01)
*A61F 2/30* (2006.01)

(52) U.S. Cl.
CPC ............... *A61F 2002/30056* (2013.01); *A61F 2002/30062* (2013.01); *A61F 2002/30303* (2013.01); *A61F 2002/30578* (2013.01); *A61F 2002/30785* (2013.01); *A61F 2002/30789* (2013.01); *A61F 2002/30838* (2013.01); *A61F 2002/30878* (2013.01); *A61F 2002/30884* (2013.01); *A61F 2002/30892* (2013.01); *A61F 2002/30899* (2013.01); *A61F 2002/4485* (2013.01); *A61F 2210/0004* (2013.01); *A61F 2310/00017* (2013.01); *A61F 2310/00023* (2013.01); *A61F 2310/00029* (2013.01); *A61F 2310/00089* (2013.01); *A61F 2310/0097* (2013.01); *A61F 2310/00113* (2013.01); *A61F 2310/00131* (2013.01); *A61F 2310/00149* (2013.01); *A61F 2310/00155* (2013.01); *A61F 2310/00293* (2013.01); *A61F 2310/00796* (2013.01); *A61F 2310/00976* (2013.01)

(56) References Cited

U.S. PATENT DOCUMENTS

| | | | |
|---|---|---|---|
| 4,911,718 A | 3/1990 | Lee et al. | |
| 5,071,437 A | 12/1991 | Steffee | |
| 5,607,424 A * | 3/1997 | Tropiano | 623/17.16 |
| 5,713,899 A * | 2/1998 | Marnay et al. | 623/17.11 |
| 5,972,032 A | 10/1999 | Lopez et al. | |
| 5,984,967 A | 11/1999 | Zdeblick et al. | |
| 6,066,175 A * | 5/2000 | Henderson et al. | 623/17.11 |
| 6,090,143 A | 7/2000 | Meriwether et al. | |
| 6,231,615 B1 | 5/2001 | Preissman | |
| 6,235,059 B1 * | 5/2001 | Benezech et al. | 623/17.16 |
| 6,264,695 B1 | 7/2001 | Stoy | |
| 6,309,420 B1 | 10/2001 | Preissman | |
| 6,461,359 B1 * | 10/2002 | Tribus et al. | 606/247 |
| 6,511,510 B1 * | 1/2003 | de Bruijn et al. | 623/23.56 |
| 6,541,022 B1 | 4/2003 | Murphy et al. | |
| 6,558,424 B2 * | 5/2003 | Thalgott | 623/17.16 |
| 6,582,467 B1 | 6/2003 | Teitelbaum et al. | |
| 6,613,091 B1 | 9/2003 | Zdeblick et al. | |
| 6,767,928 B1 * | 7/2004 | Murphy et al. | 521/51 |
| 6,837,905 B1 * | 1/2005 | Lieberman | 623/17.16 |
| 7,004,971 B2 | 2/2006 | Serhan et al. | |
| 7,008,452 B2 | 3/2006 | Hawkins | |
| 7,083,624 B2 | 8/2006 | Irving | |
| 7,087,200 B2 | 8/2006 | Taboas et al. | |
| 7,112,222 B2 | 9/2006 | Fraser et al. | |
| 7,112,417 B2 | 9/2006 | Vyakarnam et al. | |
| 7,166,570 B2 | 1/2007 | Hunter et al. | |
| 7,174,282 B2 | 2/2007 | Hollister et al. | |
| 7,628,816 B2 * | 12/2009 | Magerl et al. | 623/17.16 |
| 2002/0026244 A1 | 2/2002 | Trieu | |
| 2002/0082597 A1 * | 6/2002 | Fraser | 606/61 |
| 2002/0156529 A1 | 10/2002 | Li et al. | |
| 2003/0006534 A1 | 1/2003 | Taboas et al. | |
| 2003/0069718 A1 | 4/2003 | Hollister et al. | |
| 2003/0074096 A1 | 4/2003 | Das et al. | |
| 2003/0125739 A1 | 7/2003 | Bagga et al. | |
| 2003/0167091 A1 * | 9/2003 | Scharf | 623/17.11 |
| 2004/0034428 A1 | 2/2004 | McKay | |
| 2004/0034430 A1 * | 2/2004 | Falahee | 623/17.16 |
| 2004/0265385 A1 * | 12/2004 | West | 424/484 |
| 2005/0055099 A1 | 3/2005 | Ku | |
| 2005/0240267 A1 * | 10/2005 | Randall et al. | 623/17.11 |
| 2005/0260173 A1 * | 11/2005 | Hall | 424/93.7 |
| 2005/0283255 A1 | 12/2005 | Geremakis et al. | |
| 2006/0030851 A1 * | 2/2006 | Bray et al. | 606/69 |
| 2006/0195100 A1 * | 8/2006 | Kirschman | 606/69 |
| 2006/0276925 A1 | 12/2006 | Lin et al. | |
| 2007/0016295 A1 * | 1/2007 | Boyd | 623/17.11 |
| 2007/0027416 A1 * | 2/2007 | Rapp | 602/5 |
| 2007/0055252 A1 * | 3/2007 | Blain et al. | 606/69 |
| 2007/0213828 A1 * | 9/2007 | Trieu et al. | 623/17.11 |

FOREIGN PATENT DOCUMENTS

| | | |
|---|---|---|
| WO | 03/105731 A1 | 12/2003 |
| WO | 2005/011523 A2 | 2/2005 |
| WO | 2006/101837 A2 | 9/2006 |

OTHER PUBLICATIONS

International Search Report for International Application No. PCT/US07/82952.
European Patent Office Supplemental Search and Opinion for EP 07871281.7.

\* cited by examiner

DEGRADABLE CAGE COATED WITH MINERAL LAYERS FOR SPINAL INTERBODY FUSION

CROSS-REFERENCES TO RELATED APPLICATIONS

This application claims priority from U.S. Provisional Patent Application No. 60/855,235 filed Oct. 30, 2006.

STATEMENT REGARDING FEDERALLY SPONSORED RESEARCH

Not Applicable.

BACKGROUND OF THE INVENTION

1. Field of the Invention

This invention relates to cages for facilitating the fusion of adjacent bones or adjacent bone surfaces, and more particularly to degradable cages for spinal interbody fusion.

2. Description of the Related Art

Back pain resulting from instability of the spinal system is a rapidly growing condition in the United States. Spinal fusion procedures are expected to grow from over 400,000 procedures in 2004 to 550,000 procedures in 2010. This is driven by an aging population, increasing obesity, and increased patient education and awareness of the fusion procedures. While current segmental spinal fusion relieves pain by eliminating spinal instability, complications associated with conventional metallic cages, including; difficulty of revisions, increased adjacent level disc disease due to increased loading, implant migration or failure, imaging artifacts, stress shielding, and limited bone grafting significantly reduce the efficacy of the interbody fusion. Non-degradable polymeric materials such as polyetheretherketone (PEEK) have been introduced as new cage materials as they are radiotransparent and compliant and can enhance postoperative image modality and fusion rate. However, since clinically reliable reports of using these cages are scarce, concerns still remain that synovitis and the lymphatic spread of non-absorbable polymer debris may be found after intra-articular procedures (see Cho et al., "Preliminary experience using a polyetheretherketone (PEEK) cage in the treatment of cervical disc disease" *Neurosurgery* 52(3):693 2003 and *Neurosurgery* 51:1343 2002; and Parsons et al., "Carbon fiber debris within the synovial joint. A time-dependent mechanical and histologic study", *Clinical Orthopaedics & Related Research* 1985:69-76).

It has been reported that spine musculoskeletal impairments, including degenerative disc disease, stenosis, spondylolysis, and/or spondylolisthesis, represent more than one-half (51.7% or 15.4 million incidents) of the musculoskeletal impairments reported in the United States. In the United States, 279,000 spinal arthrodesis were performed in 1990, with 26 lumbar fusions performed per 100,000 people (see Andersson, "Epidemiological features of chronic low-back pain", *Lancet* 354:581-5, 1999). In 1995, approximately 160,000 spinal fusion surgeries were performed (see Praemer et al. "Musculoskeletal Conditions in the United States" Park Ridge: American Academy of Orthopaedic Surgeons, 1999). A recent report in 2000 (see Sanhu, "Anterior lumbar interbody fusion with osteoinductive growth factors", *Clinical Orthopaedics and Related Research* 371:56-60, 2000) revealed that in the United States alone approximately 360,000 patients underwent some type of spinal arthrodesis. The use of cage devices has become an adjunct to interbody fusion for degenerative disorders of the lumbar spine. However, current metallic cages are associated with excessive rigidity that increases incidence of postoperative complications such as stress-shielding, the migration or dislodgement of the cage, pseudoarthrosis, or the combined adverse symptoms (see van Dijk et al. "The effect of cage stiffness on the rate of lumbar interbody fusion: An in vivo model using poly(L-lactic acid) and titanium cages", *Spine* 27:682-8, 2002). Metallic cages can also interfere with visual assessment of arthrodesis and the integrity of the spinal canal and neural foramina due to image artifact. The stress-shielded environment resulting from excessive metallic cage stiffness lowers intracage pressure (see Kanayama et al., "In vitro biomechanical investigation of the stability and stress-shielding effect of lumbar interbody fusion devices", *Journal of Neurosurgery* 93:259-65, 2000), leading to subsequent decreased mineralization, bone resorption, and significant bone mineral density decrease in long-term (see Cunningham et al., "A quantitative densitometric study investigating the stress-shielding effects of interbody spinal fusion devices: Emphasis on long-term fusions in thoroughbred racehorses", *Trans Orthop Res Soc* 23:250, 1998).

Many current efforts to reduce these complications have concentrated on using poly ($\alpha$-hydroxy) ester polymers that have much lower stiffness than metallic materials to fabricate conventional cage designs (see, Kandziora et al., "Biomechanical analysis of biodegradable interbody fusion cages augmented with poly(propylene glycol-co-fumaric acid)", *Spine* 27:1644-51, 2002; Toth et al., "Evaluation of 70/30 poly (L-lactide-co-D,L-lactide) for use as a resorbable interbody fusion cage", *Journal of Neurosurgery* 97:423-32, 2002; van Dijk et al., "Bioabsorbable poly-L-lactic acid cages for lumbar interbody fusion: three-year follow-up radiographic, histologic, and histomorphometric analysis in goats", *Spine* 27:2706-14, 2002). Degradable cages possess a number of significant advantages over non-degradable materials including eventual removal of all foreign material that could cause nerve root irritation, alleviation of stress-shielding effects and reduce adjacent level disc disease, and removal of imaging artifact. Nevertheless, the mere replacement of base material from original designs might lead to cages that cannot provide adequate stability since biodegradable polymers have less stiffness/strength than permanent materials and this reduced stiffness/strength will be further compromised over the degradation time. Furthermore, primary degradation products of these poly ($\alpha$-hydroxy) acids form a low pH environment that can inhibit osteogenesis. It has been shown that even small pH shifts can significantly affect bone marrow stromal cell (BMSC) function of proliferation and differentiation (see Kohn et al., "Effects of pH on human bone marrow stromal cells in vitro: Implications for tissue engineering of bone", *Journal of Biomedical Materials Research* 60:292-9, 2002) since the growth and development of osteoblasts are linked to regulation of pH and acidity of the extracellular microenvironment (see Chakkalakal et al., "Mineralization and pH relationships in healing skeletal defects grafted with demineralized bone matrix" *Journal of Biomedical Materials Research* 28:1439-43, 1994; Green "Cytosolic pH regulation in osteoblasts", *Mineral and Electrolyte Metabolism* 20:16-30, 1994; Kaysinger et al., "Extracellular pH modulates the activity of cultured human osteoblasts", *Journal of Cellular Biochemistry* 68:83-913-15, 1998). Therefore, although degradable polymer cages offer significant potential advantages over non-degradable cages, there are also significant hurdles to overcome including the maintenance of adequate mechanical properties and reduction of acidic degradation products.

With various bone graft substitutes emerging as biological inducers to achieve successful arthrodesis, delivery within a restricted volume becomes critical. Among a variety of promising bone graft substitutes, bone growth factors and cell-based approaches particularly require suitable delivering vehicles (see Helm et al. "Bone graft substitutes for the promotion of spinal arthrodesis", *Neurosurg Focus* 10:1-5, 2000). Several recombinant human bone morphogenic proteins (rh-BMPs) have been approved for certain clinical applications, and they are commonly delivered through an absorbable collagen sponge to effectively achieve arthrodesis by osteoinduction. However, current delivering approaches are associated with the inability to directly deliver bone morphogenic proteins for bone regeneration.

The only commercially available delivery system at this moment for bone morphogenic protein consists of collagen sponges soaked in bone morphogenic protein solutions that contain bone morphogenic protein at concentrations over a million times higher than what is physiologically found in the human body. The release of the bone morphogenic protein in this fashion obviously consists of a very large bolus quantity of which all its effects are unknown. Reports have shown that bone morphogenic protein can also cause an initial osteolysis of surrounding bone secondary to what is thought to be an initial drain of osteogenic cells from surrounding bone towards the bone morphogenic protein soaked sponges. This can initially weaken surrounding bone structures thus promoting subsidence of any supporting implants. Furthermore, a high concentration of bone morphogenic protein has been shown to cause swelling of surrounding soft tissue with resultant swallowing and breathing difficulty. Another disadvantage of uncontrolled release of bone morphogenic protein is the ectopic formation of bone. Bone formation distal from the intended site of osteogenesis can result in radiculopathy as well as intradural bone formation.

Primary requirements in developing biodegradable cages are assuring that porous degradable cages can withstand surgical impaction forces, can carry in vivo spinal forces initially and up to the time bony fusion is achieved (normally 3-6 months), and have degradation products that will not adversely affect bone regeneration. However, bone tissue engineering within degradable constructs invokes two new requirements in addition to the primary degradable cage requirements delineated above. The first is osteoconductivity, which is the ability to promote and support ingrowth of bone-forming cells. Among the most common strategies to confer osteoconductivity to an orthopedic implant material involves coating with a calcium-phosphate-based mineral film similar to bone mineral. These films have a well-characterized positive effect on the ingrowth and proper function of bone-forming cell types, including osteoblasts and osteoblast precursors. U.S. Pat. No. 6,767,928 (which is incorporated herein by reference as if fully set forth herein) shows that calcium-phosphate mineral coatings can be grown on porous polymer scaffolds, and that the mineral coatings positively influence bone tissue growth. The technology used to grow these mineral coatings mimics the process of natural bone mineralization, and the coatings have a structure, mineral phase, and elemental composition that is similar to human bone mineral (see also, Bunker et al., "Ceramic thin film formation on functionalized interfaces through biomimetic processing", *Science* 264:48-55, 1994; Mann et al., "Crystallization and inorganic-organic interfaces—biominerals and biomimetic synthesis", *Science* 261: 1286-92, 1993; Murphy et al., "Bioinspired growth of crystalline carbonate apatite on biodegradable polymer substrata", *J Am Chem Soc* 124:1910-7, 2002; and Ohgushi et al., "Stem cell technology and bioceramics: from cell to gene engineering", *J Biomed Mater Res* 48:913-27, 1999). These "bone-like" mineral coatings have been shown to significantly enhance osteoconductivity of orthopedic implant materials (see Ohgushi et al.; Hench, "Bioceramics: From concept to clinic", *Journal of the American Ceramic Society* 74:1487-510, 1991; Murphy et al., "Bone regeneration via a mineral substrate and induced angiogenesis", *J Dent Res* 83:204-10, 2004). In addition to their osteoconductivity, mineral coatings also represent a potential vehicle for delivery of osteogenic growth factors (see Seeherman et al., "Bone morphogenetic protein delivery systems", *Spine* 27:S16-23, 2002). Multiple bone growth factors, including BMP-2, IGF-1 and TGF-β (see Gittens et al., "Imparting bone mineral affinity to osteogenic proteins through heparin-bisphosphonate conjugates", *J Control Release* 98:255-68, 2004; Gorski et al., "Is all bone the same? Distinctive distributions and properties of non-collagenous matrix proteins in lamellar vs. woven bone imply the existence of different underlying osteogenic mechanisms", *Crit Rev Oral Biol Med* 9:201-23, 1998; Gorski et al., "Bone acidic glycoprotein-75 is a major synthetic product of osteoblastic cells and localized as 75- and/or 50-kDa forms in mineralized phases of bone and growth plate and in serum", *J Biol Chem* 265:14956-63, 1990; Liu et al., "Bone morphogenetic protein 2 incorporated into biomimetic coatings retains its biological activity", *Tissue Eng* 10:101-8, 2004; Matsumoto et al., "Hydroxyapatite particles as a controlled release carrier of protein", *Biomaterials* 25:3807-12, 2004; and Sachse et al., "Osteointegration of hydroxyapatite-titanium implants coated with nonglycosylated recombinant human bone morphogenetic protein-2 (BMP-2) in aged sheep", *Bone* 37:699-710, 2005) have been shown to interact strongly with bone-like mineral substrates. Therefore, it is possible that calcium phosphate mineral substrates can be coated with growth factors, and these factors can subsequently be presented to bone-forming cells growing into a scaffold construct. Previous studies have demonstrated that it is indeed possible to use hydroxyapatite minerals as template substrates to bind and release bone growth factors, particularly BMP-2, and that the bound growth factors induce bone ingrowth in vivo (see Gittens et al.; and Sachse et al.).

Notwithstanding the foregoing advances in tissue engineering, there is still a need for improved cages for facilitating the fusion of adjacent bones such as vertebrae, or adjacent bone surfaces such as in an open fracture.

SUMMARY OF THE INVENTION

The inventors have developed the necessary design and fabrication techniques to create optimized degradable spine fusion cages to fulfill the load carrying requirement and have also created prototype cages from a biodegradable polymer polycaprolactone (PCL) using Solid Free-Form Fabrication (SFF) techniques. This pilot work has helped characterize the designed biodegradable cages and define the most appropriate design for incorporating with therapeutic bioactive agents to facilitate spinal arthrodesis.

The structurally tailored design that is able to fulfill the mechanical load bearing requirements is incorporated with innovative mineralization processes to enhance the bioactivity of the spinal implant. The mineral coated PCL cage is also believed to have superior binding capacity and persistent delivery of therapeutic molecules such as bone morphogenetic proteins (BMP) compared to current approaches such as collagen sponges.

In one aspect, the present invention provides a cage for facilitating fusion of adjacent bones or adjacent bone surfaces. The cage includes a designed porous microstructure comprising a biocompatible and, if desired, biodegradable material selected from polymeric materials, metallic materials, ceramic materials and mixtures thereof; an osteoconductive mineral coating on at least a portion of the designed porous microstructure; and a bioactive agent associated with the biocompatible material and/or the coating. The bioactive agent is present on the cage in amount that induces ossification between the adjacent bones or adjacent bone surfaces.

In another aspect, the present invention provides a cage for facilitating fusion of adjacent vertebrae. The cage includes (i) a plurality of spaced apart walls or other designed porous microstructure formed from a biocompatible, biodegradable polymeric material (e.g., polycaprolactone), (ii) an integrated fixation projection which could include an integrated plate, peg, or spike, (iii) an osteoconductive mineral coating (e.g., a calcium compound) on at least a portion of the walls, and (iv) a bioactive agent associated with the polymer and/or the coating. The bioactive agent is present in amount that induces ossification between the adjacent vertebrae.

As used herein, a "biocompatible" material is one which stimulates only a mild, often transient, implantation response, as opposed to a severe or escalating response. As used herein, a "biodegradable" material is one which decomposes under normal in vivo physiological conditions into components which can be metabolized or excreted. As used herein, a bioactive agent is "associated" with the polymer and/or the coating if the bioactive agent is directly or indirectly, physically or chemically bound to the polymer and/or the coating. A bioactive agent may be physically bound to the polymer and/or the coating by entrapping, imbedding or otherwise containing a bioactive agent within the polymer and/or the coating network structure. A bioactive agent may be chemically bound to the polymer and/or the coating by way of a chemical reaction wherein a bioactive agent is covalently or ionically bonded to the polymer and/or the coating. Thus, various techniques for associating a bioactive agent in or on the polymer and/or the coating are contemplated herein.

A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, cells, enzymes, organic catalysts, ribozymes, organometallics, proteins (e.g., bone morphogenetic proteins including recombinant human bone morphogenetic proteins), demineralized bone matrix, bone marrow aspirate, glycoproteins, peptides, polyamino acids, antibodies, nucleic acids, steroidal molecules, antibiotics, antimycotics, cytokines, fibrin, collagen, fibronectin, vitronectin, hyaluronic acid, growth factors (e.g., transforming growth factors and fibroblast growth factor), carbohydrates, statins, oleophobics, lipids, extracellular matrix and/or its individual components, pharmaceuticals, and therapeutics.

In one example version of the invention, the bioactive agent is selected from bone morphogenetic proteins, transforming growth factors, fibroblast growth factor, insulin-like growth factor, platelet derived growth factor, and vascular endothelial growth factor. Preferably, the bioactive agent is a bone morphogenetic protein (BMP). Most preferably, the bioactive agent is BMP-2, BMP-4, BMP-7, BMP-14, growth and development factor-5 (GDF-5), or platelet rich plasma (PRP).

These and other features, aspects, and advantages of the present invention will become better understood upon consideration of the following detailed description, drawings and appended claims.

BRIEF DESCRIPTION OF THE DRAWINGS

FIG. 3 shows scanning electron microscope (SEM) micrographs showing large scale pore structure of polycaprolactone scaffolds without calcium phosphate coating (left, top right), and with calcium phosphate coating (bottom right).

Like reference numerals will be used to refer to like or similar parts from Figure to Figure in the following description.

DETAILED DESCRIPTION OF THE INVENTION

Figure 1A:
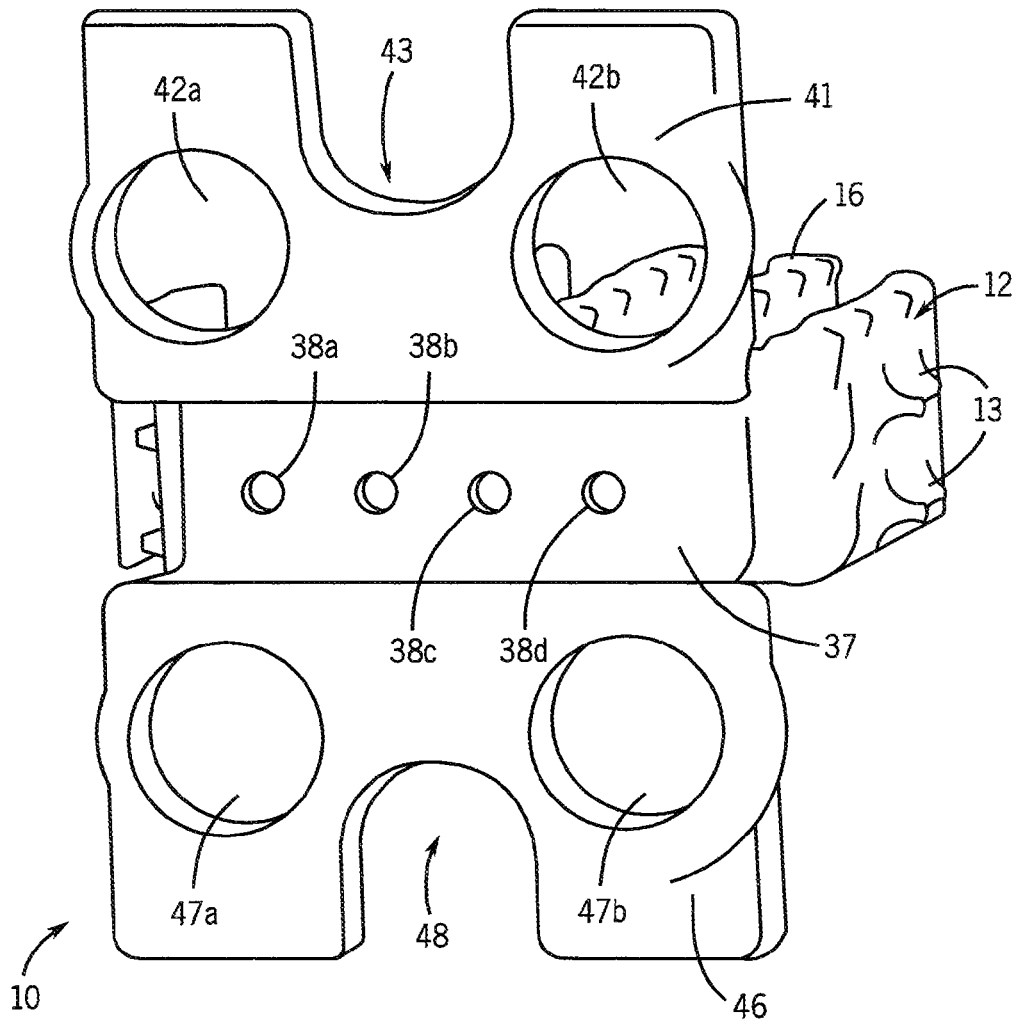
FIG. 1A shows a right rear perspective view of a cervical spine fusion cage design with an integrated anterior fixation plate and designed microstructure.

One purpose of the proposed invention is to develop a simple and flexible method that enhances osteogenesis to achieve spine arthrodesis induced by biologically active bone morphogenetic proteins released from osteoconductive, biodegradable spine fusion cages. The working hypothesis of these studies is that bone morphogenetic proteins incorporated in a calcium phosphate mineral coating on a polycaprolactone spine fusion cage will induce more rapid and complete bone regeneration when compared with bone morphogenetic proteins delivered from a collagen sponge placed within a cage. The approach we use to grow calcium phosphate mineral coatings on polycaprolactone cages is a low temperature process, which will allow for incorporation of active bone morphogenetic proteins after mineral growth via surface binding. The resulting composite cage will then contain biologically active growth factors, which will be released upon mineral dissolution and/or degradation of the cage. The degradable cage loaded with bone morphogenetic protein will be implanted into intervertebral space of a Yucatan minipig model and compared to the current mode of bone morphogenic protein delivery, which involves rapid release from a collagen sponge carrier placed within the cage.

The invention of the designed degradable interbody fusion system may represent a transition from passive support of bone graft material within the intervertebral space (e.g., traditional dense cage designs) to a more aggressive strategy of spinal tissue engineering.

1. Interbody Fusion Cage Design

U.S. Patent Application Publication No. 2003/0069718 (which is incorporated herein by reference as if fully set forth herein and corresponds to U.S. Pat. No. 7,174,282) provides a design methodology for creating biomaterial scaffolds with internal porous architectures that meet the need for mechanical stiffness and strength and the need for connected porosity for cell migration and tissue regeneration. The design methods of U.S. 2003/0069718 combine image-based design of structures with homogenization theory to compute effective physical property dependence on material microstructure. Optimization techniques are then used to compute the optimal geometry. The final optimized scaffold geometry voxel topology is then combined with a voxel data set describing the three dimensional anatomic scaffold shape which may be obtained by magnetic resonance (MR) images or combined MR and computed tomography (CT) images. Density variations within the anatomic scaffold voxel database are used as a map to guide where different optimized scaffold voxel topologies are substituted. The final voxel representation of the anatomically shaped scaffold with optimized interior architecture is then converted automatically by software into either a surface representation or wire frame representation for fabrication of the scaffold by way of solid free form fabrication or casting.

In the present invention, the interbody fusion cages will be designed based on a CT scan of a cadaver Yucatan minipig lumbar spine. The integrated topology optimization technique will be utilized to create a cage design based on the techniques of U.S. 2003/0069718. We will run the optimization program to predict densities at different time points in the degradation profile, thus incorporating degradation into the design. In the degradation design, the density in each element is weighted by the degradation profile. The proposed optimization method creates a density distribution map for selected time points during degradation. These different density distributions are then superposed using a time lasting and degrading modulus factor. The time lasting factor: defined as $T_{wt}=(T_{total}-T_{current})/T_{total}$, where $T_{total}$ is total degradation duration, $T_{current}$ is the time at a selected point. This factor accounts for the influence of the time past implantation on reinforcement of the scaffold architecture. The degrading modulus factor is defined as $E_{wt}=E^0{}_{ijkl}(T_{current})/E^0{}_{ijkl}(T_{initial})$. The factor indicates the weight percentage of the original material equivalent to the superposed material densities based on the degrading modulus at selected time points. The optimal global/macroscopic density distribution for degradation design is then interpreted into $X_{pw}=\Sigma X_{pt}T_{wt}E_{wt}$, where $X_{pw}$ is the final fraction of the base material, and $X_{pt}$ is the temporary fraction of the reduced/degraded modulus corresponding to a selected time point. The approach created cages designed to retain desired stiffness after a specified degradation period.

The resolution of the global degradation topology design is too coarse, however, to give the specific microstructure that will be located within that point of the scaffold. Furthermore, since we would like the microstructure to have specific elastic properties at a fixed porosity, homogenization based topology optimization is used to design the microstructure (see Hollister et al. "Optimal design and fabrication of scaffolds to mimic tissue properties and satisfy biological constraints", *Biomaterials* 23:4095-103, 2002; and Lin et al. "A novel method for internal architecture design to match bone elastic properties with desired porosity", *Journal of Biomechanics* 37:623-36, 2004). The microscopic or 2nd scale topology optimization approach gives the specific microstructure design that achieves a desired compliance while matching the predicted volume fraction of the macroscopic or 1st level topology optimization.

In the interior cage microstructure design, the image-based methods as in U.S. 2003/0069718 can be used to design an interior cage with internal architecture optimized to match target bone Young's moduli. In particular, the minimum and maximum interior cage Young's moduli could be set to 1 and 15 GPa, respectively, to reflect the Young's modulus of available scaffold material ranging from biopolymers (E=1 GPa) to bioceramics (E=15 GPa). This can optimize strain for bone growth. Also, the modulus ranges for trabecular bone and intevertebral disc that we want to target for fusion and disc repair are: Bone: 30-200 MPa, and Intervertebral Disc: 0.4-10 MPa.

In addition to the interior cage microstructure design, we also design the fixation structure for the cage using image-based methods as in U.S. 2003/0069718. Specifically, for cervical spine fusion, we have developed a cage integrated with anterior plate fixation. One example of this design is shown in FIGS. 1A and 1B.

Figure 1B:
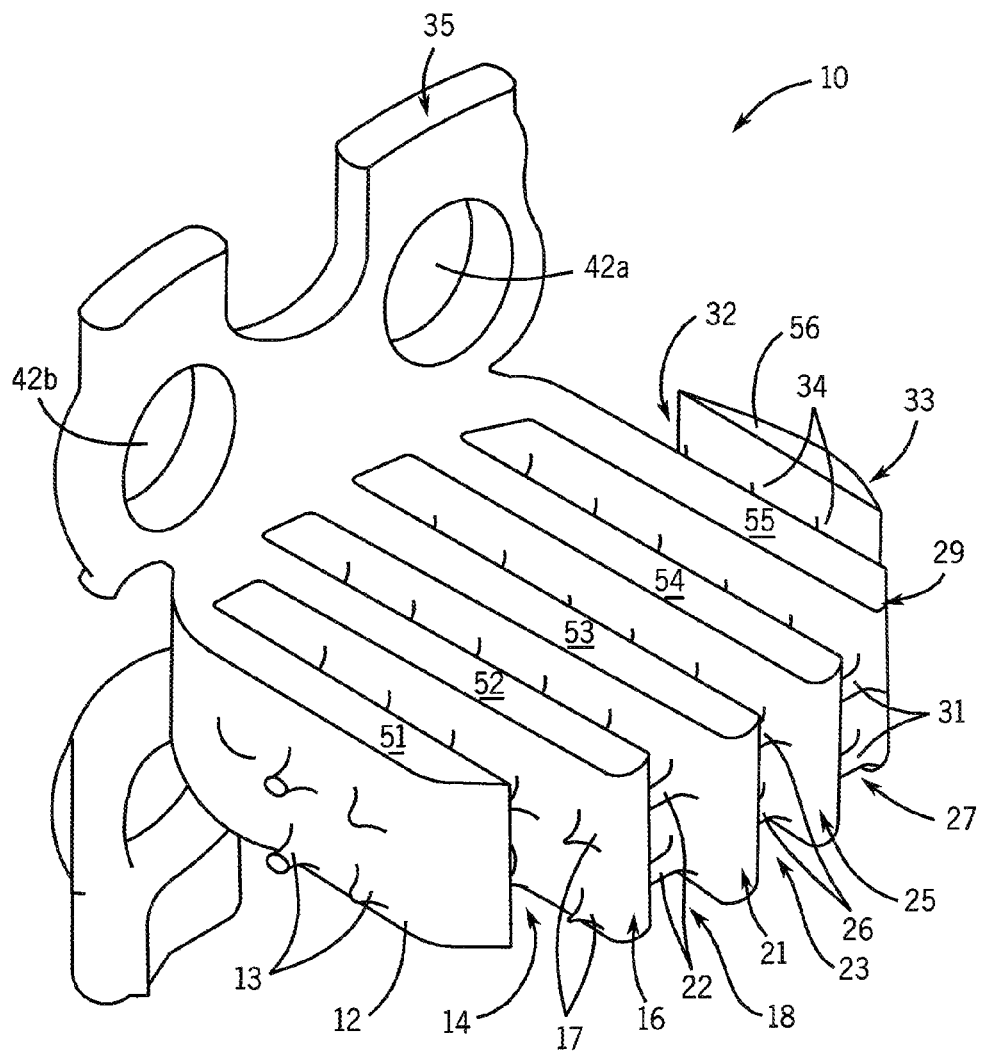
FIG. 1B shows a top front left perspective view of the cervical spine fusion cage design of FIG. 1A.

Referring now to FIGS. 1A and 1B, there is shown an image-based porous microstructure design of a cervical spine fusion cage 10. The cage 10 has a first vertical wall 12 having a substantially rectangular transverse vertical cross section. The first wall 12 has projections 13 extending substantially perpendicularly from a vertical side surface of the first wall 12. A first space 14 is created between the first wall 12 and a second vertical wall 16 having a substantially rectangular transverse vertical cross section. The second wall 16 has projections 17 extending substantially perpendicularly from a vertical side surface of the second wall 16. A second space 18 is created between the second wall 16 and a third vertical wall 21 having a substantially rectangular transverse vertical cross section. The third wall 21 has projections 22 extending substantially perpendicularly from a vertical side surface of the third wall 21. A third space 23 is created between the third wall 21 and a fourth vertical wall 25 having a substantially rectangular transverse vertical cross section. The fourth wall 25 has projections 26 extending substantially perpendicularly from a vertical side surface of the fourth wall 25. A fourth space 27 is created between the fourth wall 25 and a fifth vertical wall 29 having a substantially rectangular transverse vertical cross section. The fifth wall 29 has projections 31 extending substantially perpendicularly from a vertical side surface of the fifth wall 29. A fifth space 32 is created between the fifth wall 29 and a sixth vertical wall 33 having a substantially rectangular transverse vertical cross section. The sixth wall 33 has projections 34 extending substantially perpendicularly from a vertical side surface of the sixth wall 33.

Still referring to FIGS. 1A and 1B, the cage 10 has a fixation plate 35 having a central section 37 with throughholes 38a, 38b, 38c, 38d. The walls 12, 16, 21, 25, 29, 33 are integral with the central section 37 of the fixation plate 35. The walls 12, 16, 21, 25, 29, 33 are substantially perpendicular with the fixation plate 35. The fixation plate 35 includes a top section 41 that is slightly offset outward from the central section 37 of the fixation plate 35. The top section 41 includes spaced apart fastener holes 42a, 42b, and a top central U-shaped cutaway section 43. The fixation plate 35 includes a bottom section 46 that is slightly offset outward from the central section 37 of the fixation plate 35. The bottom section 46 includes spaced apart fastener holes 47a, 47b, and a bottom central inverted U-shaped cutaway section 48. When used in spinal fusion, the walls 12, 16, 21, 25, 29, 33 of the cage 10 would be positioned in the intervertebral space created by removal of the intervertebral disc between adjacent vertebrae. Fasteners would be inserted in fastener holes 42a, 42b for anterior attachment to a first upper vertebra, and fasteners would be inserted in fastener holes 47a, 47b for anterior attachment to an adjacent second lower vertebra. Top end surfaces 51, 52, 53, 54, 55, 56 of the walls 12, 16, 21, 25, 29, 33 would contact a lower surface of the first upper vertebra, and opposite bottom end surfaces of the walls 12, 16, 21, 25, 29, 33 would contact an upper surface of the second lower vertebra. The walls 12, 16, 21, 25, 29, 33 thereby provide mechanical load bearing support between the first upper vertebra and the second lower vertebra.

The vertical dimensions of the walls 12, 16, 21, 25, 29, 33 can be adjusted accordingly for various different intervertebral distances. Likewise, the horizontal length from the fixation plate 35 to the opposite outer end of each of the walls 12, 16, 21, 25, 29, 33 can be adjusted such that the ends of the walls 12, 16, 21, 25, 29, 33 do not extend outward beyond the perimeter of the first upper vertebra and the second lower vertebra. Similarly, the width of each of the walls 12, 16, 21, 25, 29, 33, and the width of each of the interior spaces 14, 18, 23, 27, and the width of each projection 13, 17, 22, 26, 31, 34 can be adjusted to control degradation characteristics. Optionally, the projections 13, 17, 22, 26, 31, 34 could attach adjacent walls. Also, the vertical and horizontal dimensions of the fixation plate 35 and the location of the fastener holes 42a, 42b, 47a, 47b can be varied to ensure proper location of the fastener holes 42a, 42b, 47a, 47b adjacent the first upper vertebra and the second lower vertebra for securing the cage 10 to the first upper vertebra and the second lower vertebra. By varying the vertical and horizontal dimensions of the walls 12, 16, 21, 25, 29, 33 and the vertical and horizontal dimensions of the fixation plate 35, different size cages 10 can be provided for selection by a surgeon.

Because certain polymeric materials are degraded by physiological fluid, the throughholes 38a, 38b, 38c, 38d are placed in the central section 37 of the fixation plate 35 to allow fluid into the interior spaces 14, 18, 23, 27 of the cage 10 to degrade the walls 12, 16, 21, 25, 29, 33 comprising the interior section of the cage 10. The throughholes serve to minimize any problems associated with tissue blockage of fluid. Optionally, flaps (not shown) can be provided on the top section 41 and the bottom section 46 of the fixation plate 35 to prevent backing out of the fasteners (e.g., fixation screws). In one embodiment, the fixation screws can be formed using the same biocompatible and biodegradable material with an osteoconductive mineral coating, and a bioactive agent associated with the biodegradable material and/or the coating.

The cage 10 can comprise a porous biocompatible and biodegradable (if desired) porous material selected from polymeric materials, metallic materials, ceramic materials and mixtures thereof. In one example embodiment, the spine fusion cage 10 is formed from polycaprolactone, a biocompatible and biodegradable polymer. However, other polymers such as polylactide, polyglycolide, poly(lactide-glycolide), poly(propylene fumarate), poly(caprolactone fumarate), polyethylene glycol, and poly(glycolide-co-caprolactone) may be advantageous for forming the cage 10.

An osteoconductive mineral coating is formed on at least a portion of the cage 10. The osteoconductive mineral coating can comprises a plurality of discrete mineral islands, or the mineral coating can be formed on the entire surface of the cage 10. In one example form, the osteoconductive mineral coating comprises a substantially homogeneous mineral coating. In one example embodiment, the mineral coatings may be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, and the like. The mineral coating may also include a plurality of layers having distinct dissolution profiles to control dissolution order, kinetics and bioactive delivery properties. Under physiological conditions, the solubility of calcium phosphate materials are as follows: amorphous calcium phosphate>dicalcium phosphate>octacalcium phosphate>tricalcium phosphate>hydroxyapatite. Thus, a plurality of various calcium phosphate layers can provide a broad range of dissolution patterns. Incorporation of blank layers (i.e., calcium phosphate layers not containing any bioactive agent) can provide for delayed release. Also, the incorporation of layers having different concentrations of bioactive agent can provide for varying release rates.

A bioactive agent can be associated with uncoated biocompatible material forming the cage 10 and/or the mineral coated portions of the cage 10. Different release rates of the bioactive agent would be possible from uncoated and coated areas of the cage 10. While various bioactive agents listed above are suitable for use with the cage 10, in one example embodiment, the bioactive agent is selected from bone morphogenetic proteins, demineralized bone matrix, bone marrow aspirate, and mixtures thereof. Bone morphogenetic proteins have been shown to be excellent at growing bone and powdered recombinant human BMP-2 is available in certain commercial products. Demineralized bone matrix includes osteoinductive proteins (e.g., bone morphogenetic proteins), and can be used in a particle or fiber form. Bone marrow aspirate contains osteoprogenitor cells, and the patient's bone marrow can be readily harvested with a needle.

The bioactive agent is present in amount that induces ossification between the adjacent bones or adjacent bone surfaces. The amount of bioactive agent included on uncoated and/or coated areas of the cage 10 will depend on a variety of factors including the nature of the bioactive agent, the osteoinductive potential of the bioactive agent, and the nature of the carrier material (e.g., the biocompatible material forming the cage 10 or the mineral coating on the cage 10). Investigations have shown that a 1-100 ng/ml concentration of BMP can induce osteogenesis; and in one example, the BMP in the present invention can be released from the cage 10 in a time frame that varies from 10-50 days. Therefore, without intending to limit the invention in any way, in the case of bone morphogenetic proteins, it is contemplated that in one example a concentration of about 10-5000 ng of bone morphogenetic protein per $cm^3$ of material would be suitable for inducing ossification between the adjacent bones or adjacent bone surfaces.

Various regions of the cage 10 can include the coatings and associated bioactive agent. For example, top and bottom end regions of the walls 12, 16, 21, 25, 29, 33 that are positioned near the opposed vertebrae can be coated with continuous or islands of the coating and associated bioactive agent so that bone growth is induced, while interior sections of the cage may not include coatings and associated bioactive agent in order to promote growth of fibrous tissue. As an exemplary illustration, top end surfaces 51, 52, 53, 54, 55, 56 in FIG. 1B could include a continuous mineral coating and associated bioactive agent so that bone fixation to the adjacent vertebra is induced, while regions near the projections 13, 17, 22, 26, 31, 34 may not include the coating and associated bioactive agent so fibrous growth is promoted in this region.

Preferably, the bioactive agent (e.g., bone morphogenetic protein) is associated with uncoated biocompatible material forming the cage 10 and/or the mineral coated portions of the cage 10 prior to inserting the walls 12, 16, 21, 25, 29, 33 of the cage 10 in the intervertebral disc space. For example, a bone morphogenetic protein may be chemically bonded (e.g., ionically or covalently bonded) to a calcium phosphate coating at a manufacturing site, or alternatively a bone morphogenetic protein may be chemically bonded to the calcium phosphate coating by a surgeon before and/or after implantation. The surgeon can reconstitute powdered bone morphogenetic protein with sterile water and apply the reconstituted powdered bone morphogenetic protein to the cage 10. It is contemplated that the calcium phosphate layer can be selected to best accept BMP-2 applied by a surgeon.

Various optional features of the cage 10 would be beneficial. Because placement of the cage 10 may be performed using a medical imaging device and techniques (e.g., fluoroscopic observation), the cage 10 may further include at least one marking including a tracer that provides enhanced visibility via the medical imaging device. For example, non-limiting examples of radiopaque materials for enhanced visibility during fluoroscopy include barium sulfate, tungsten, tantalum, zirconium, platinum, gold, silver, stainless steel, titanium, alloys thereof, and mixtures thereof. Radiopaque markings can be used as an alignment aid in verifying the proper positioning of the cage 10. Also, the cage 10 may include a region of no material or radiolucent material such that the region forms an imaging window for enhanced visibility through the imaging window via a medical imaging device. The image-based design methods as in U.S. 2003/0069718 are beneficial as the imaging window can be arranged in the cage without comprising the strength of the cage.

For lumbar fusion, we have developed a transforaminal lumbar interbody fusion (TLIF) cage with an integrated lateral plate for fixation. Thus, only a one step procedure is needed to implant a cage with associated fixation. One example of this design is shown in FIG. 5.

Figure 5:
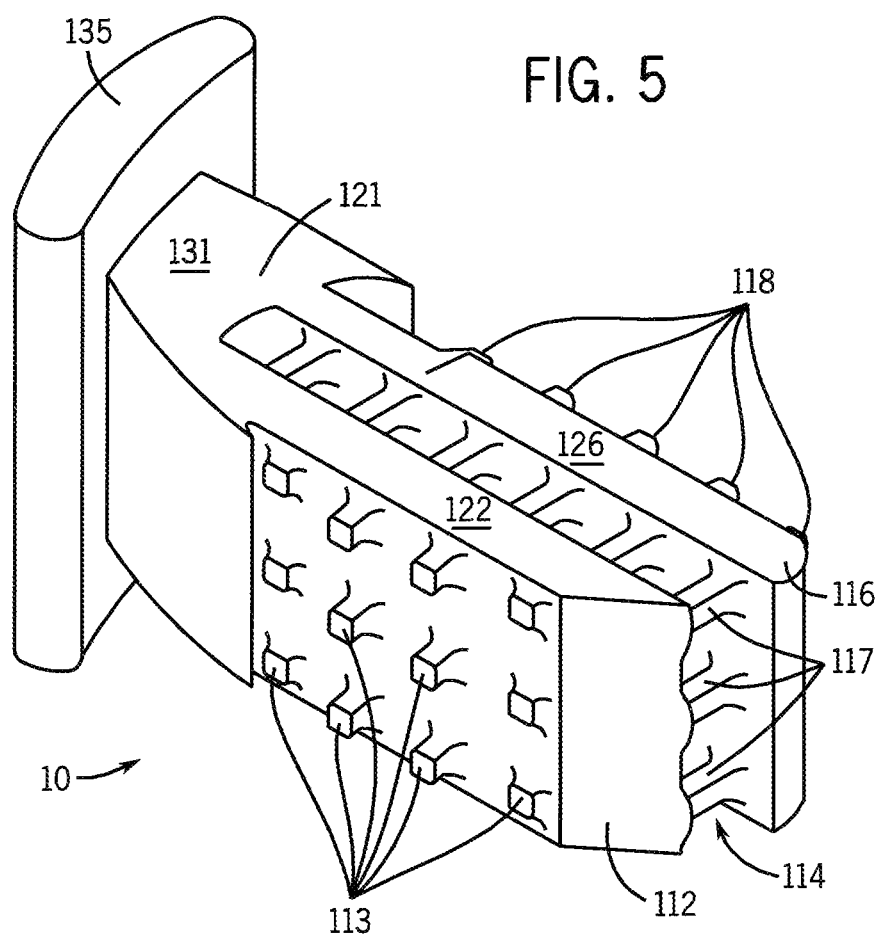
FIG. 5 shows a top front left perspective view of a lumbar spine fusion cage design with an integrated lateral plate for fixation.

Looking now at FIG. 5, there is shown an image-based porous microstructure design of a transforaminal lumbar interbody fusion cage 110. The cage 110 has a first vertical wall 112 having a substantially rectangular transverse vertical cross section. The first wall 112 has projections 113 extending substantially perpendicularly from a vertical side surface of the first wall 112. A first space 114 is created between the first wall 112 and a second vertical wall 116 having a substantially rectangular transverse vertical cross section. The second wall 116 has projections 117 extending substantially perpendicularly from a vertical side surface of the second wall 116. The second wall 116 also has projections 118 extending substantially perpendicularly from an opposite vertical side surface of the second wall 116. The first wall 112 and the second wall 116 are connected to a base section 121.

Still referring to FIG. 5, the cage 110 has a slightly arcuate fixation plate 135. The walls 112, 116 and the base section 121 are substantially perpendicular with the fixation plate 135. The fixation plate 135 can include spaced apart fastener holes (not shown) in a top section of the fixation plate 135 and spaced apart fastener holes (not shown) in a bottom section of the fixation plate 135 as in the cage 10 of FIGS. 1A and 1B. The fixation plate 135 can also include through-holes (as in the cage 10 of FIGS. 1A and 1B) in the central section of the fixation plate 135 to allow fluid into the interior space 114 of the cage 110 to degrade the walls 112, 116 comprising the interior section of the cage 110. When used in spinal fusion, the walls 112, 116, of the cage 110 would be positioned in the intervertebral space created by removal of the intervertebral disc between adjacent vertebrae. Fasteners would be used for lateral attachment of the fixation plate 135 to a first upper vertebra, and fasteners would be used for lateral attachment of the fixation plate 135 to an adjacent second lower vertebra. Top end surfaces 122, 126, 131 of the walls 112, 116 and the base section 121 would contact a lower surface of the first upper vertebra, and opposite bottom end surfaces of the walls 112, 116 and the base section 121 would contact an upper surface of the second lower vertebra. The walls 112, 116 and the base section 121 thereby provide mechanical load bearing support between the first upper vertebra and the second lower vertebra. As in the cage 10, the vertical and horizontal dimensions of the walls 112, 116, and the vertical and horizontal dimensions of the fixation plate 135 can be varied so that different size cages 110 can be provided for selection by a surgeon.

The cage 110 comprise a porous biocompatible, biodegradable (if desired) material selected from polymeric materials, metallic materials, ceramic materials and mixtures thereof. In one example embodiment, the spine fusion cage 110 is formed from polycaprolactone, a biocompatible and biodegradable polymer. However, other polymers such as polylactide, polyglycolide, poly(lactide-glycolide), poly (propylene fumarate), poly(caprolactone fumarate) and poly (glycolide-co-caprolactone) may be advantageous for forming the cage 110.

An osteoconductive mineral coating is formed on at least a portion of the cage 110. The osteoconductive mineral coating can comprises a plurality of discrete mineral islands, or the mineral coating can be formed on the entire surface of the cage 110. In one example form, the osteoconductive mineral coating comprises a substantially homogeneous mineral coating. In one example embodiment, the mineral coatings may be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, and the like. The mineral coating may also include a plurality of layers having distinct dissolution profiles to control dissolution order, kinetics and bioactive delivery properties as in the cage 10.

A bioactive agent can be associated with uncoated biocompatible material forming the cage 110 and/or the mineral coated portions of the cage 110. Different release rates of the bioactive agent would be possible from uncoated and coated areas of the cage 110. The bioactive agent is present in amount that induces ossification between the adjacent bones. While various bioactive agents listed above are suitable for use with the cage 110, in one example embodiment, the bioactive agent is selected from bone morphogenetic proteins, demineralized bone matrix, bone marrow aspirate, and mixtures thereof.

Various optional features of the cage 110 would be beneficial. For example, at least one marking including a tracer that provides enhanced visibility via a medical imaging device can be located on the cage 110. Specifically, at least one radiopaque marking that provides enhanced visibility via a fluoroscope can be located on the cage 110. The cage 110 can include a region of no material or radiolucent material such that the region forms an imaging window for enhanced visibility through the imaging window via a medical imaging device. Also, the cage can include at least one marking for alignment during implantation.

The methods of U.S. Patent Application Publication No. 2006/0276925 also provide a design methodology for creating biomaterial scaffolds with internal porous architectures that meet the need for mechanical stiffness and strength and the need for connected porosity for cell migration and tissue regeneration. The methods of U.S. 2006/0276925 (which is incorporated herein by reference as if fully set forth herein) can be used to generate a lumbar spine interbody fusion cage with a designed periodic microstructure that attains desired stability (displacements <0.9 mm.), while maintaining compliance to avoid stress shielding and a large porosity for biofactor delivery.

2. Cage Fabrication

Figure 2:
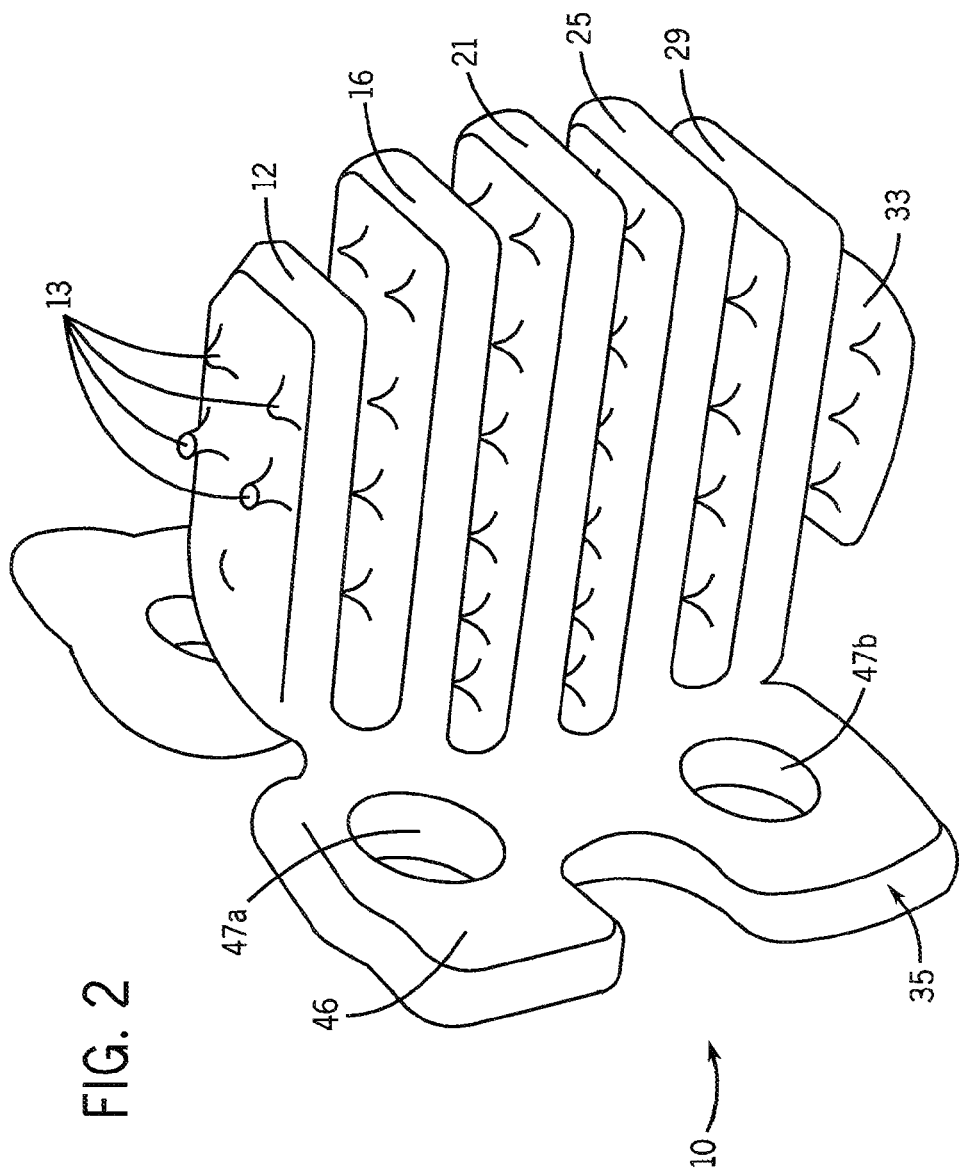
FIG. 2 shows a bottom perspective view of a cervical spine cage prototype with integrated anterior plate made using the design of FIGS. 1A and 1B.

Once the intervertebral scaffolding image-design dataset is created, it can be automatically converted into a surface representation in .stl file format (stereolithography triangular facet data). This makes it possible to fabricate the intervertebral scaffolding from any type of Solid Free-Form Fabrication (SFF) system using either direct or indirect methods. Direct SFF methods include, but are not limited to: (1) Selective Laser Sintering (SLS); (2) Stereolithography (SLA); (3) Fused Deposition Modeling (FDM); and (4) Selective Laser Melting (SLM). In the present invention, both of the conventional design of the tapered cage and the new design by degradation topology optimization will be exported to an EOS Formega P 100 machine (3D Systems, Valencia, Calif., USA) in .stl file format, and will be used to construct scaffolds by SLS processing of ϵ-polycaprolactone powder. This particular form of polycaprolactone has a melting point of 60° C., a molecular weight in the range of 35,000 to 100,000 Daltons, and particle size distribution in the 25-100 µm range. However, nanoscale particle sizes are also suitable in place of the microscale particle sizes. SLS processing of the polycaprolactone powder will be conducted by preheating the powder to 49.5° C. and scanning the laser (450 µm focused beam diameter) at 4.5 Watts power and 1.257 m/s (49.5 inches/s) scan speed. Cages will be built layer-by-layer using a powder layer thickness of 100 µm. After SLS processing is completed, the cages will be allowed to cool inside the machine process chamber for approximately 1 hour and will be then removed from the part bed. Excess powder surrounding the cages will be brushed off and the cages will be finally cleaned by blowing compressed air and physically removing unsintered powder from the cage interstices by insertion of a 1 millimeter diameter wire. FIG. 2 shows a fabricated polycaprolactone cervical cage prototype built using the SLS process. (The reference numerals of FIGS. 1A and 1B have been applied to FIG. 2.) In an alternative method, calcium-phosphate-based particles or fibers are included with the polycaprolactone powder before sintering such that the calcium-phosphate-based particles or fibers are dispersed in the final formed cage. The particle sizes for the calcium-phosphate-based particles can be nanoscale or microscale.

Figure 3:
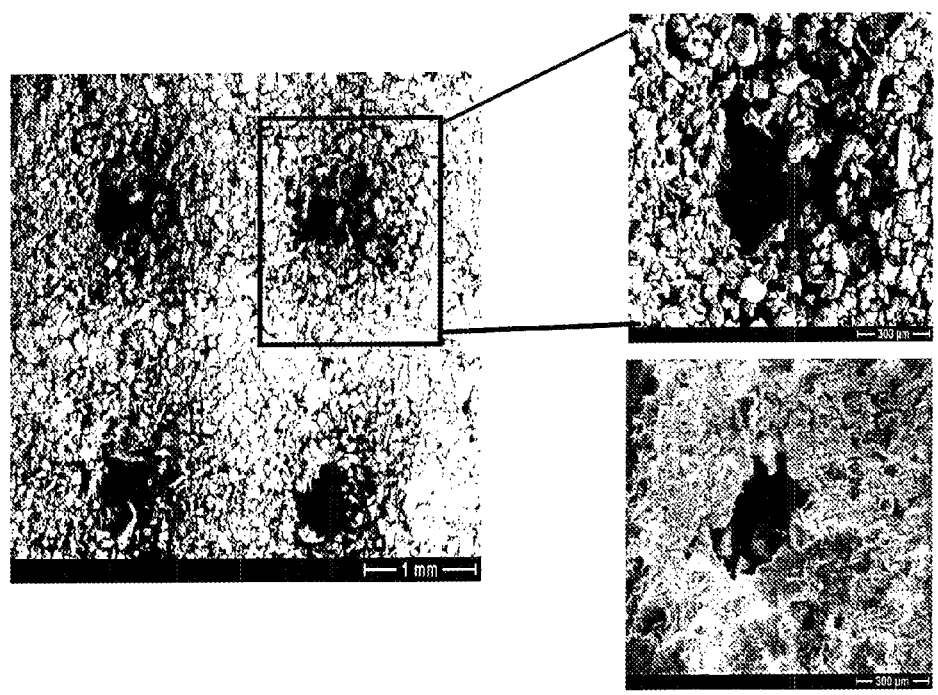
FIG. 3 shows the results of coating polycaprolactone with calcium phosphate. In particular.
Figure 4:
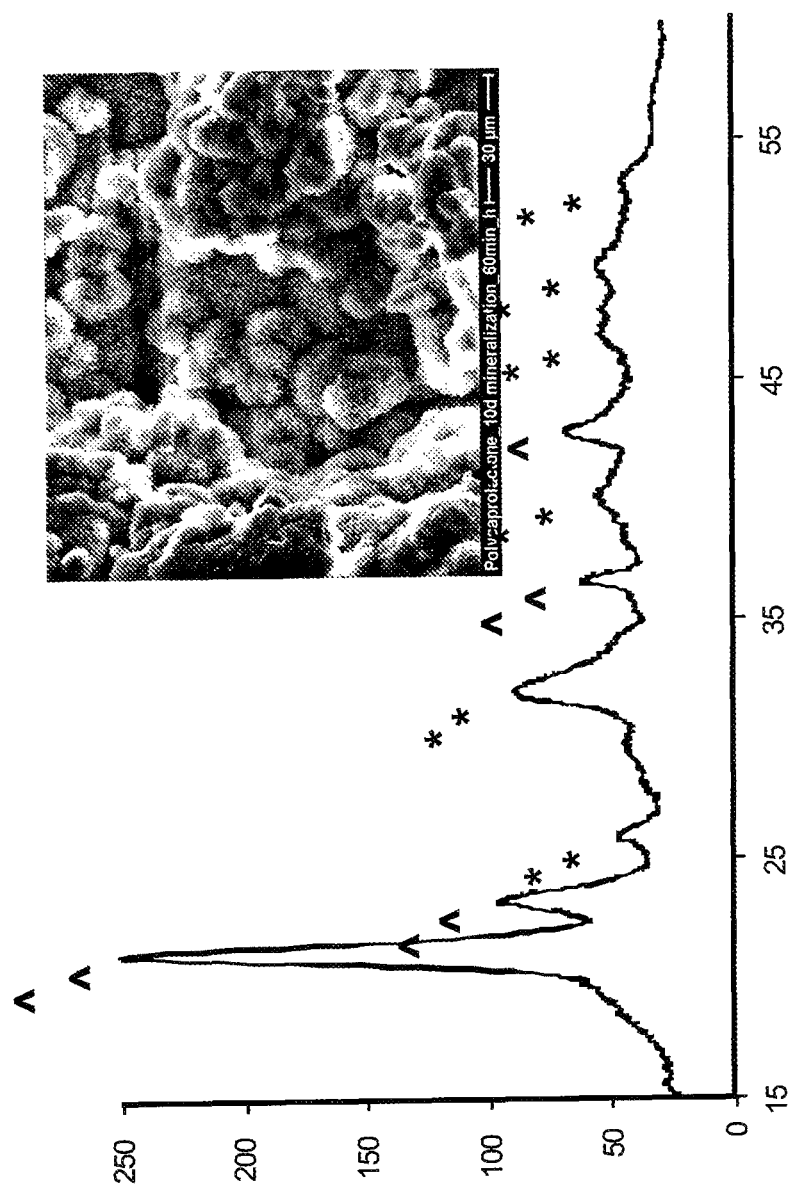
FIG. 4 shows an X-ray diffraction spectrum showing hydroxyapatite (*) grown on a polycaprolactone (^) scaffold. The inset is a high magnification SEM image of a calcium phosphate coating grown on a polycaprolactone scaffold.

3. Develop and Characterize Calcium Phosphate-Based Mineral Coatings on Polycaprolactone Cages To induce formation of a calcium phosphate-based mineral layer, polycaprolactone samples were incubated in modified simulated body fluid (mSBF) solutions for mineral nucleation and growth. The mSBF solution contained the ionic constituents of blood plasma, with double the concentrations of calcium and phosphate ions, and was held at physiologic temperature and pH 6.8. The growth of calcium phosphate-based minerals, specifically bone-like minerals, on bioresorbable polymer matrices using mSBF incubation has been demonstrated (see, Lin et al. "A novel method for internal architecture design to match bone elastic properties with desired porosity", *Journal of Biomechanics* 37:623-36, 2004; Murphy et al., "Bioinspired growth of crystalline carbonate apatite on biodegradable polymer substrata", *J Am Chem Soc* 124:1910-7, 2002; and Murphy et al., "Effects of a bone-like mineral film on phenotype of adult human mesenchymal stem cells in vitro", *Biomaterials* 26:303-10, 2005). Looking at FIGS. 3 and 4, the results of coating polycaprolactone with calcium phosphate are shown. FIG. 3 shows scanning electron microscope (SEM) micrographs showing large scale pore structure of polycaprolactone scaffolds without calcium phosphate coating (left, top right), and with calcium phosphate coating (bottom right). FIG. 4 shows an X-ray diffraction spectrum showing hydroxyapatite (*) grown on a polycaprolactone (Λ) scaffold. The inset is a high magnification SEM image of a calcium phosphate coating grown on a polycaprolactone scaffold. Therefore, this serves as a reliable method for growth of mineral coatings.

Mineral formation in mSBF will also be tracked by analyzing changes in solution calcium concentration using a calcium sensitive electrode (Denver Instrument, Denver, Colo.). After their growth, the mineral matrices will be dissolved and analyzed for calcium and phosphate ion content to quantify mineral formation, and the mineral crystals will be analyzed morphologically and compositionally using a scanning electron microscope (SEM) with a Noran SiLi detector for elemental analysis. The chemical composition will be further analyzed using Fourier transform infrared spectroscopy to identify phosphate bond vibrations (570 $cm^{-1}$, 962 $cm^{-1}$, and 1050 $cm^{-1}$). We will also characterize dissolution of mineral layers by measuring release of calcium and phosphate ions during incubation in tris-buffered saline at 37° C. at pH 7.4. Calcium and phosphate concentrations will be measured using previously described calorimetric assays (see Murphy et al., "Bioinspired growth of crystalline carbonate apatite on biodegradable polymer substrata", *J Am Chem Soc* 124:1910-7, 2002). Each of the characterization methods described in this section is routine in analysis of inorganic materials, and is consistent with FDA's good guidance practices for design and testing of calcium phosphate coatings (see Devices FDoGaR. Calcium phosphate coating draft guidance for preparation of FDA submissions for orthopedic and dental endosseous implants. 1997).

This indicates that it is possible to confer both osteoconductivity and osteoinductivity to orthopedic implant materials using calcium phosphate coatings. Based on the well-defined osteoconductivity and potential osteoinductivity of calcium-phosphate-based mineral coatings, we plan to utilize technology for calcium phosphate mineral growth to coat polycaprolactone spine fusion cages. This research work will primarily investigate effectiveness of utilizing the mineral coated polycaprolactone spine fusion cages to facilitate rapid bone regeneration and achieve the integrity of the new construct by spinal arthrodesis in a Yucatan minipig fusion model.

4. Incorporate Bone Morphogenetic Protein Within and Upon Growing Mineral Coatings and Evaluate Incorporation and Release Prior to in vivo experiments to test the efficacy of our fusion cages, we will undertake several in vitro studies to validate our approach. The focus of the in vitro work will be on understanding the interaction between bone morphogenetic protein BMP-2 and calcium phosphate mineral coatings, measuring the release of BMP-2 from the coatings, and confirming biological activity of released BMP-2. The following paragraphs delineate specific in vitro experiments.

Binding of BMP-2 to Mineralized PCL Scaffolds Followed by Release:

To characterize binding of BMP-2 to calcium phosphate mineral coatings, we will use $^{125}$I-labeled BMP-2 (ICN Biomedicals). Radiolabeling represents a highly sensitive and convenient method for characterizing protein binding and release (see, Murphy et al., "Bone regeneration via a mineral substrate and induced angiogenesis", *J Dent Res* 2004; 83:204-10; and Murphy et al., "Growth of continuous bonelike mineral within porous poly(lactide-co-glycolide) scaffolds in vitro", *J Biomed Mater Res* 50:50-8, 2000). Mineral coatings will be grown on polycaprolactone cages, followed by a 4 hour incubation in solutions containing 1-100 nM $^{125}$I-labeled BMP-2. Based on previous studies by Uludag and coworkers we expect that our calcium-phosphate coated scaffolds will bind BMP-2 with 50-100% efficiency in the soluble BMP-2 concentration range explored (see, Gittens et al., "Imparting bone mineral affinity to osteogenic proteins through heparin-bisphosphonate conjugates", *J Control Release* 98:255-68, 2004). The scaffolds will then be removed from solution, rinsed with serum free DMEM, and analyzed for radioactivity using a scintillation counter. To characterize subsequent release of bound BMP-2, the samples will be incubated in DMEM with 10% FBS for 14 days. Every 24 hours media will be refreshed and radioactivity in solution will be measured. Based on previous studies we expect that the release will primarily take place over the initial 7 days in solution with near zero order release kinetics (see, Gittens et al., "Imparting bone mineral affinity to osteogenic proteins through heparin-bisphosphonate conjugates", *J Control Release* 98:255-68, 2004). These experiments will also demonstrate release of a broad range of total BMP-2 from scaffolds, as the total amount of protein released will be dictated by the amount of BMP-2 present in the binding solution (1-100 nM). It is contemplated that BMP-2 forms ionic bonds to hydroxyapatite in solution. It is also contemplated that certain amino acid mineral binding fragments could be incorporated into the BMP-2 such that the mineral binding fragments form ionic bonds to hydroxyapatite in solution. Ionic binding advantageously provides suitable controlled delivery of bone morphogenetic protein through dissolution of the calcium phosphate layer or degradation of the polycaprolactone. In contrast, sponge based BMP delivery systems rely on absorption of the BMP into the sponge which makes controlled delivery difficult to attain.

Examining Biological Activity of Engineered Growth Factors:

In order to confirm the biological activity of BMP-2 after binding to, and release from, mineral layers, it will be important to use an assay that is well-defined and biologically relevant. Promotion of osteogenic differentiation of multipotent cell types is a key function of several BMPs (see Nakamura et al., "p38 mitogen-activated protein kinase functionally contributes to chondrogenesis induced by growth/differentiation factor-5 in ATDC5 cells", *Exp Cell Res* 250:351-63, 1999; Saito et al., "Activation of osteoprogenitor cells by a novel synthetic peptide derived from the bone morphogenetic protein-2 knuckle epitope", *Biochim Biophys Acta* 1651:60-7, 2003; and Saito et al., "Prolonged ectopic calcification induced by BMP-2-derived synthetic peptide", *J Biomed Mater Res A* 70A:115-21, 2004), and osteogenic induction of the mouse embryonic fibroblast cell line C3H10T1/2 by BMP-2 is well-characterized. Therefore, a C3H10T1/2 cell-based biological activity assay will be used to characterize soluble BMP-2 released from mineralized polycaprolactone scaffolds. We will expose cells to 0.1-100 ng/ml BMP-2 released from mineral layers and measure alkaline phosphatase upregulation, a hallmark of osteogenic induction by BMP-2, using a standard colorimetric assay. We will then compare these results to a standard curve that relates soluble BMP-2 concentrations (not released from scaffolds) to alkaline phosphatase upregulation, which will give the effective activity of BMP-2 released from scaffolds. We expect that the activity of the released BMP-2 will not be substantially effected by mineral binding and release, as BMPs are known to bind strongly to calcium phosphate minerals under normal conditions in vivo (see, Gorski et al., "Is all bone the same? Distinctive distributions and properties of non-collagenous matrix proteins in lamellar vs. woven bone imply the existence of different underlying osteogenic mechanisms", *Crit Rev Oral Biol Med* 9:201-23, 1998; Gorski et al., "Bone acidic glycoprotein-75 is a major synthetic product of osteoblastic cells and localized as 75- and/or 50-kDa forms in mineralized phases of bone and growth plate and in serum", *J Biol Chem* 265:14956-63, 1990).

Therefore, it can be seen that the invention provides a cage for facilitating the fusion of adjacent bones such as vertebrae, or adjacent bone surfaces, such as in an open fracture. In one form, the cage includes a plurality of spaced apart walls comprising porous polycaprolactone; an osteoconductive mineral coating (e.g., a calcium phosphate compound) on at least a portion of the walls; and a bioactive agent (e.g., a bone morphogenetic protein) associated with the polycaprolactone and/or the coating. The bone morphogenetic protein is present in amount that induces ossification between the adjacent bones or adjacent bone surfaces. Preferably, the cage also includes a fixation plate connected to at least one of the walls, wherein the fixation plate also comprises polycaprolactone.

Although the invention has been described in considerable detail with reference to certain embodiments, one skilled in the art will appreciate that the present invention can be practiced by other than the described embodiments, which have been presented for purposes of illustration and not of limitation. For instance, while the cage of the invention is advantageous in the fixation, connecting, reconstruction and/or regeneration of vertebrae, the cages of the invention would be suitable for the fusion of any adjacent bones or adjacent bone surfaces. For example, the cages of the invention could be used in the treatment of acute, open fractures in a bone (e.g., tibia), or in oral and maxillofacial bone grafting procedures. Therefore, the scope of the appended claims should not be limited to the description of the embodiments contained herein.

What is claimed is:

1. A cage for facilitating fusion of adjacent bones or fusion of adjacent bone surfaces, the cage comprising:
   a central section having a longitudinal proximal portion and a longitudinal distal portion;
   a first wall, having a first height, a first length, and a first width, wherein each of the first length and the first height is greater than the first width, wherein the first length of the first wall extends transversely from the central section, and wherein the first height of the first wall extends between the longitudinal proximal portion and the longitudinal distal portion of the central section;
   a second wall, having a second height, a second length, and a second width, wherein each of the second length and the second height is greater than the second width, wherein the second length of the second wall extends transversely from the central section, and wherein the second height of the second wall extends between the longitudinal proximal portion and the longitudinal distal portion of the central section; and
   a third wall, having a third height, a third length, and a third width, wherein each of the third length and the third height is greater than the third width, wherein the third length of the third wall extends transversely from the central section, wherein the third height of the third wall extends between the longitudinal proximal portion and the longitudinal distal portion of the central section, wherein the third wall has a first side and a second side separated by the third width, wherein the third wall is positioned between the first wall and the second wall, and wherein the first side of the third wall faces the first wall and the second side of the third wall faces the second wall, wherein each of the first wall and the second wall comprises an end portion distal to the central section, wherein the end portion of the first wall and the end portion of the second wall avoid contact with the third wall,
   wherein the central section, the first wall, the second wall, and the third wall comprise a designed porous microstructure and the designed porous microstructure further comprises a biocompatible material selected from at least one of a polymeric material, a metallic material, a ceramic material, or a mixture thereof;
   an osteoconductive mineral coating on at least a portion of the designed porous microstructure, the osteoconductive mineral coating comprising a plurality of layers, wherein each of the layers has a distinct dissolution profile;
   a bioactive agent associated with at least one of the biocompatible material or the osteoconductive mineral coating, wherein the bioactive agent being present in an amount that induces ossification between the adjacent bones or the adjacent bone surfaces; and
   a fixation plate extending from the central section.

2. The cage of claim 1, wherein at least one of the first wall, the second wall, and the third wall is coupled to the central section at a respective proximal side of the at least one of the first wall, the second wall, and the third wall.

3. The cage of claim 2, wherein at least two adjacent of the first wall, the second wall, and the third wall are not coupled to each other at a respective distal side of each of the at least two adjacent of the first wall, the second wall, and the third wall.

4. The cage of claim 1, wherein at least two of the first wall, the second wall, and the third wall comprise projections extending perpendicularly therefrom.

5. The cage of claim 4, wherein the at least two of the first wall, the second wall, and the third wall are coupled to each other by the projections.

6. The cage of claim 1, wherein the fixation plate extends from the longitudinal proximal portion of the central section.

7. The cage of claim 6, wherein the fixation plate extends orthogonally to at least one of the first wall, the second wall, and the third wall.

8. The cage of claim 1 wherein:
   the osteoconductive mineral coating comprises a plurality of discrete mineral islands.

9. The cage of claim 1 wherein:
   the osteoconductive mineral coating comprises a substantially homogeneous mineral coating.

10. The cage of claim 1 wherein:
    the bioactive agent is selected from bone morphogenetic proteins, demineralized bone matrix, bone marrow aspirate, transforming growth factors, fibroblast growth factor, insulin-like growth factor, platelet derived growth factor, vascular endothelial growth factor, growth and development factor-5, platelet rich plasma, and mixtures thereof.

11. The cage of claim 1 wherein:
    the bioactive agent is selected from bone morphogenetic proteins.

12. The cage of claim 1 wherein:
    the osteoconductive mineral coating comprises a calcium compound.

13. The cage of claim 1 wherein:
    the osteoconductive mineral coating is selected from hydroxyapatite, calcium-deficient carbonate-containing hydroxyapatite, tricalcium phosphate, amorphous calcium phosphate, octacalcium phosphate, dicalcium phosphate, calcium phosphate, and mixtures thereof.

14. The cage of claim 1 wherein:
    the biocompatible material comprises polycaprolactone.

15. The cage of claim 1, wherein the biocompatible material comprises polycaprolactone, and wherein the fixation plate comprises polycaprolactone.

16. The cage of claim 1 wherein:
    the bones are adjacent vertebrae.

17. The cage of claim 1, wherein at least one of the first wall, the second wall, and the third wall is perpendicular to the fixation plate.

18. The cage of claim 1, wherein the first wall, the second wall, and the third wall are not connected via another wall or cage element.

19. The cage of claim 1, wherein the fixation plate is positioned transverse to at least one of the first wall, the second wall, and the third wall.

20. A cage for facilitating fusion of adjacent bones or fusion of adjacent bone surfaces, the cage comprising:
    a central section having a longitudinal proximal portion and a longitudinal distal portion;
    a first wall, having a first height, a first length, and a first width, wherein each of the first length and the first height is greater than the first width, wherein the first length of the first wall extends transversely from the central section, and wherein the first height of the first wall extends between the longitudinal proximal portion and the longitudinal distal portion of the central section;
    a second wall, having a second height, a second length, and a second width, wherein each of the second length and the second height is greater than the second width, wherein the second length of the second wall extends transversely from the central section, and wherein the second height of the second wall extends between the longitudinal proximal portion and the longitudinal distal portion of the central section; and a third wall, having a third height, a third length, and a third width, wherein each of the third length and the third height is greater than the third width, wherein the third length of the third wall extends transversely from the central section, wherein the third height of the third wall extends between the longitudinal proximal portion and the longitudinal distal portion of the central section, wherein the third wall has a first side and a second side separated by the third width, wherein the third wall is positioned between the first wall and the second wall, and wherein the first side of the third wall faces the first wall and the second side of the third wall faces the second wall, wherein each of the first wall and the second wall comprises an end portion distal to the central section, wherein the end portion of the first wall and the end portion of the second wall avoid contact with the third wall, wherein the central section, the first wall, the second wall, and the third wall comprise a designed porous microstructure, and the designed porous microstructure further comprises a biocompatible material selected from at least one of a polymeric material, a metallic material, a ceramic material, or a mixture thereof;

an osteoconductive mineral coating on at least a portion of the designed porous microstructure, wherein the osteoconductive mineral coating comprises a plurality of layers including a calcium compound, at least two of the layers having a different concentration of a bioactive agent associated with the calcium compound such that release rate of the bioactive agent varies as the layers dissolve in physiological fluid; wherein each of the plurality of layers comprises a distinct dissolution profile;

a bioactive agent associated with at least one of the biocompatible material or the osteoconductive mineral coating, wherein the bioactive agent being present in an amount that induces ossification between the adjacent bones or the adjacent bone surfaces; and a fixation plate extending from the central section.

21. A cage for facilitating fusion of adjacent bones or fusion of adjacent bone surfaces, the cage comprising:

a central section having a longitudinal proximal portion and a longitudinal distal portion;

a first wall, having a first height, a first length, and a first width, wherein each of the first length and the first height is greater than the first width, wherein the first length of the first wall extends transversely from the central section, and wherein the first height of the first wall extends between the longitudinal proximal portion and the longitudinal distal portion of the central section;

a second wall, having a second height, a second length, and a second width, wherein each of the second length and the second height is greater than the second width, wherein the second length of the second wall extends transversely from the central section, and wherein the second height of the second wall extends between the longitudinal proximal portion and the longitudinal distal portion of the central section; and a third wall, having a third height, a third length, and a third width, wherein each of the third length and the third height is greater than the third width, wherein the third length of the third wall extends transversely from the central section, wherein the third height of the third wall extends between the longitudinal proximal portion and the longitudinal distal portion of the central section, wherein the third wall has a first side and a second side separated by the third width, wherein the third wall is positioned between the first wall and the second wall, and wherein the first side of the third wall faces the first wall and the second side of the third wall faces the second wall, wherein each of the first wall and the second wall comprises an end portion distal to the central section, wherein the end portion of the first wall and the end portion of the second wall avoid contact with the third wall, wherein the central section, the first wall, the second wall, and the third wall comprise a designed porous microstructure, and the designed porous microstructure further comprises a biocompatible material selected from at least one of a polymeric material, a metallic material, a ceramic material, or a mixture thereof;

an osteoconductive mineral coating on at least a portion of the designed porous microstructure, wherein the osteoconductive mineral coating comprises a plurality of layers including a calcium compound, at least two of the layers having a different calcium compound associated with a bioactive agent such that release rate of the bioactive agent varies as the layers dissolve in physiological fluid; wherein each of the plurality of layers comprises a distinct dissolution profile;

a bioactive agent associated with at least one of the biocompatible material or the osteoconductive mineral coating, wherein the bioactive agent being present in an amount that induces ossification between the adjacent bones or the adjacent bone surfaces; and a fixation plate extending from the central section.

22. A cage for facilitating fusion of adjacent bones or fusion of adjacent bone surfaces, the cage comprising:

a central section, having a longitudinal proximal portion and a longitudinal distal portion;

a first wall, having a first height, a first length, and a first width, wherein each of the first length and the first height is greater than the first width, wherein the first length of the first wall extends transversely from the central section, and wherein the first height of the first wall extends between the longitudinal proximal portion and the longitudinal distal portion of the central section;

a second wall, having a second height, a second length, and a second width, wherein each of the second length and the second height is greater than the second width, wherein the second length of the second wall extends transversely from the central section, and wherein the second height of the second wall extends between the longitudinal proximal portion and the longitudinal distal portion of the central section; and a third wall, having a third height, a third length, and a third width, wherein each of the third length and the third height is greater than the third width, wherein the third length of the third wall extends transversely from the central section, wherein the third height of the third wall extends between the longitudinal proximal portion and the longitudinal distal portion of the central section, wherein the third wall has a first side and a second side separated by the third width, wherein the third wall is positioned between the first wall and the second wall, and, wherein the first side of the third wall faces the first wall and the second side of the third wall faces the second wall, wherein each of the first wall and the second wall comprises an end portion distal to the central section, wherein the end portion of the first wall and the end portion of the second wall avoid contact with the third wall, wherein the central section, the first wall, the second wall, and the third wall comprise a designed porous microstructure, and the designed porous microstructure further comprises a biocompatible material selected from at least one of a polymeric material, a metallic material, a ceramic material, or a mixture thereof;

an osteoconductive mineral coating on at least a portion of the designed porous microstructure, wherein the osteoconductive mineral coating comprises a plurality of layers including a calcium compound, at least two of the layers having a different bioactive agent associated with the calcium compound such that release rate of the bioactive agent varies as the layers dissolve in physiological fluid; wherein each of the plurality of layers comprises a distinct dissolution profile;

a bioactive agent associated with at least one of the biocompatible material or the osteoconductive mineral coating, wherein the bioactive agent being present in an amount that induces ossification between the adjacent bones or the adjacent bone surfaces; and a fixation plate extending from the central section.

23. A cage for facilitating fusion of vertebrae, the cage comprising:

a fixation plate;

a central section having a longitudinal proximal portion and a longitudinal distal portion;

a first wall, having a first height, a first length, and a first width, wherein each of the first length and the first height is greater than the first width, wherein the first length of the first wall extends transversely from the central section, and wherein the first height of the first wall extends between the longitudinal proximal portion and the longitudinal distal portion of the central section;

a second wall, having a second height, a second length, and a second width, wherein each of the second length and the second height is greater than the second width, wherein the second length of the second wall extends transversely from the central section, and wherein the second height of the second wall extends between the longitudinal proximal portion and the longitudinal distal portion of the central section; and a third wall, having a third height, a third length, and a third width, wherein each of the third length and the third height is greater than the third width, wherein the third length of the third wall extends transversely from the central section, wherein the third height of the third wall extends between the longitudinal proximal portion and the longitudinal distal portion of the central section, wherein the third wall has a first side and a second side separated by the third width, wherein the third wall is positioned between the first wall and the second wall, and wherein the first side of the third wall faces the first wall and the second side of the third wall faces the second wall, wherein each of the first wall and the second wall comprises an end portion distal to the central section, wherein the end portion of the first wall and the end portion of the second wall avoid contact with the third wall, wherein the fixation plate extending from the central section;

an osteoconductive mineral coating on at least a portion of at least one of the walls, the osteoconductive mineral coating comprising a plurality of layers, wherein each of the layers has a distinct dissolution profile; and a bioactive agent associated with at least one of a polymeric material or the osteoconductive mineral coating, wherein the bioactive agent being present in amount that induces ossification between the vertebrae.

24. The cage of claim 23 wherein:
the polymeric material is porous polycaprolactone.

25. The cage of claim 23 wherein:
the bioactive agent is selected from bone morphogenetic proteins.

26. The cage of claim 23 wherein:
the osteoconductive mineral coating comprises a calcium compound.

27. The cage of claim 23, wherein the fixation plate comprises the polymeric material.

28. The cage of claim 23 wherein:
at least one of the first wall, the second wall, and the third wall comprises a projection extending transversely therefrom.

29. The cage of claim 23 further comprising:
at least one marking including a tracer that provides enhanced visibility via a medical imaging device.

30. The cage of claim 23 wherein:
the cage includes a region of no material or radiolucent material such that the region forms an imaging window for enhanced visibility through the imaging window via a medical imaging device.

31. A cage for facilitating fusion of vertebrae, the cage comprising:

a fixation plate;

a central section having a longitudinal proximal portion and a longitudinal distal portion;

a first wall, having a first height, a first length, and a first width, wherein each of the first length and the first height is greater than the first width, wherein the first length of the first wall extends transversely from the central section, and wherein the first height of the first wall extends between the longitudinal proximal portion and the longitudinal distal portion of the central section;

a second wall, having a second height, a second length, and a second width, wherein each of the second length and the second height is greater than the second width, wherein the second length of the second wall extends transversely from the central section, and wherein the second height of the second wall extends between the longitudinal proximal portion and the longitudinal distal portion of the central section; and a third wall, having a third height, a third length, and a third width, wherein each of the third length and the third height is greater than the third width, wherein the third length of the third wall extends transversely from the central section, wherein the third height of the third wall extends between the longitudinal proximal portion and the longitudinal distal portion of the central section, wherein the third wall has a first side and a second side separated by the third width, wherein the third wall is positioned between the first wall and the second wall, and wherein the first side of the third wall faces the first wall and the second side of the third wall faces the second wall, wherein each of the first wall and the second wall comprises an end portion distal to the central section, wherein the end portion of the first wall and the end portion of the second wall avoid contact with the third wall, wherein the fixation plate extending from the central section;

an osteoconductive mineral coating on at least a portion of at least one of the walls, wherein the osteoconductive mineral coating comprises a plurality of layers including a calcium compound, a bioactive agent associated with a polymeric material and/or the mineral coating, the bioactive agent being present in an amount that induces ossification between the vertebrae;

wherein at least two of the layers have a different concentration of the bioactive agent associated with the calcium compound such that release rate of the bioactive agent varies as the layers dissolve in physiological fluid; wherein each of the plurality of layers comprises a distinct dissolution profile.

32. The cage of claim 31 wherein:

the calcium compound is selected from hydroxyapatite, calcium-deficient carbonate-containing hydroxyapatite, tricalcium phosphate, amorphous calcium phosphate, octacalcium phosphate, dicalcium phosphate, calcium phosphate, and mixtures thereof, and the bioactive agent is selected from bone morphogenetic proteins.

* * * * *